United States Patent [19]

Rainin et al.

[11] 4,139,469
[45] Feb. 13, 1979

[54] FLUID CONTROL MECHANISM

[75] Inventors: Kenneth Rainin, Alamo; Emery Major, Larkspur, both of Calif.

[73] Assignee: Altex Scientific, Inc., Berkeley, Calif.

[21] Appl. No.: 761,014

[22] Filed: Jan. 21, 1977

[51] Int. Cl.² .............................................. B01D 15/08
[52] U.S. Cl. .................... 210/136; 137/512; 137/544; 210/198 C; 210/446
[58] Field of Search ............... 210/117, 136, 430–432, 210/446, 448, 198 C; 55/420; 137/511, 512, 512.2, 544

[56] References Cited

U.S. PATENT DOCUMENTS

| | | | |
|---|---|---|---|
| 1,310,686 | 7/1919 | Wood | 210/136 |
| 3,661,167 | 5/1972 | Hussey | 137/512 X |
| 3,693,804 | 9/1972 | Grover | 210/446 X |
| 3,771,659 | 11/1973 | Fraser | 55/386 |
| 3,933,652 | 1/1976 | Weichselbaum | 210/446 |
| 3,985,021 | 10/1976 | Achener et al. | 210/198 C |

*Primary Examiner*—John Adee
*Attorney, Agent, or Firm*—Bielen and Peterson

[57] ABSTRACT

A fluid control mechanism utilizing a housing having an opening or tunnel through the interior of the same. The housing provides at least one chamber communicating with the housing opening. A seat positions within the housing opening and the chamber. A plug, adapted to occupy the seat and close to restricted passage, positions within the first chamber. Particulate filter means comprising a pressure deformable section which includes a passage to the housing opening partially filled by a relatively rigid filter element. A gap in the filter means passage allows compression of the deformable section.

9 Claims, 3 Drawing Figures

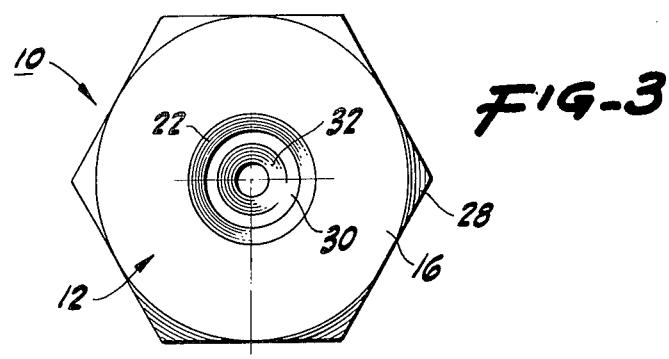
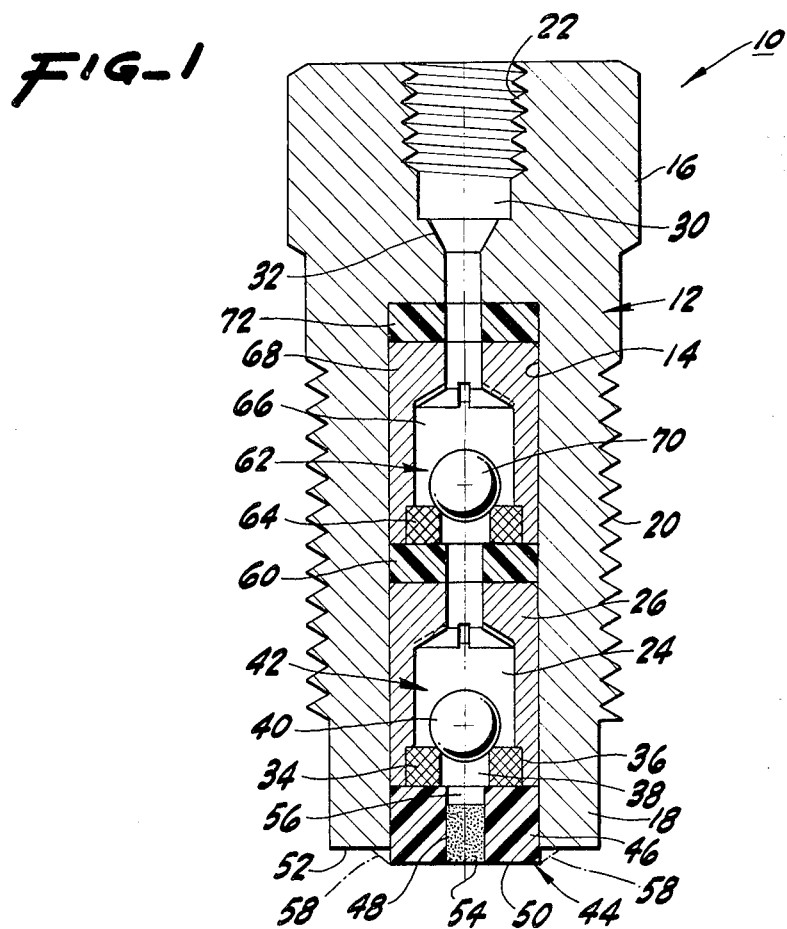
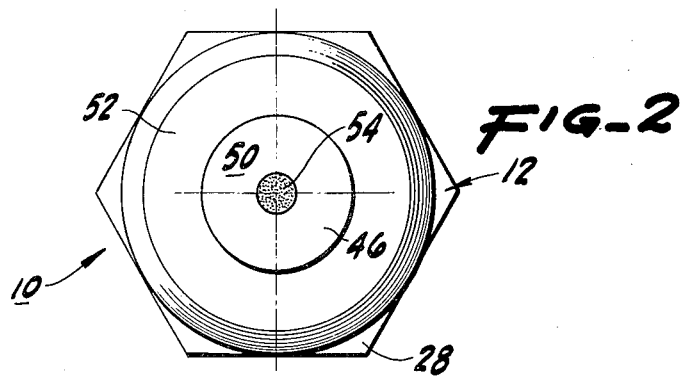

FLUID CONTROL MECHANISM

BACKGROUND OF THE INVENTION

The present invention relates to a novel fluid control mechanism for the transporting of fluids under pressure.

Fluids such as liquids may be forced through a system such as a liquid chromatography separation apparatus, by using high performance and high pressure pumps. In particular, reciprocating pumps are often employed for this purpose because of the very high pressures attainable therewith. In general, the action of the liquid-transferring parts of these pumps is the same, a cylindrical piston, plunger, or bucket being caused to pass back and forth in a cylinder. The device is equipped with valves for inlet and discharge of the liquid being pumped from the piston chamber. Usually a series of check valves automatically operate in a predetermined manner coordinated with the motions of the piston's or pistons' delivery of fluid.

Where a very high back pressure is encountered during fluid pumping proper check functioning is imperative. Maintenance of the check valve components must be meticulously performed in liquid chromatography systems to obtain accurate analysis of the fluids being separated. In this regard, preventive maintenance such as cleaning of mechanical components, prior filtering of the solvent, and other tasks have been the prior methods of control in a chromatography system.

SUMMARY OF THE INVENTION

In accordance with the present invention a novel fluid control mechanism for fluids under pressure is provided.

The mechanism includes a housing of rigid material having a bore or opening therethrough. The exterior of the housing may be sealable and may have an external threadable portion for this purpose. The housing contains a valve including a chamber communicating with the housing opening such that fluids may flow through the chamber as well as the housing opening.

A seat or valve seat positions with the housing opening and is constructed with a restricted passage which communicates with the chamber and housing opening. In other words, the seat is within the flow of fluid through the chamber within the housing opening. Preferably, the seat lies immediately adjacent the housing chamber. A plug which may be formed in the configuration of a spherical object is enclosed within the chamber and is adapted to occupy the seat to close the restricted passage therethrough. The plug may be spring loaded or biased toward seating under a preselected spring tension.

Filter means for preventing passage of particulate matter through the chamber and the seat's restricted passage, is also placed in the housing opening.

The filter means would be placed to intercept the fluid passing through the housing to prevent particulate fouling of the plug seat and chamber. In this manner, the fluid flowing through the chamber would not contaminate the working of the valve formed by the plug and seat. In particular, the filter means comprises a pressure deformable section tightly fitted into the housing opening. This pressure deformable section possesses a passage through itself, much in the same manner as the seat, communicating with the housing opening. However, the passage is only partially filled by the filter element, thus forming a gap or hiatus within the passage. This expedient permits the compression of the deformable member, and consequent cold flow thereof, as well as affording protection for the rigid filter element during insertion of the housing into a fluid forcing apparatus ie: a pump head. The deformable member affords a superior seal upon the application of pressure. The pressure deformable section would protrude from the housing opening initially to the exterior of the housing. After the application of sealing pressure, for resistance the pressure generated by the threading of the housing into a pump head, the deformable member would at least be flush with the exterior of the housing.

The housing chamber may be provided by a separate slidable member disposed within the housing. A washer may be placed adjacent the slidable member to absorb the compression on the deformable member seat and slidable member.

A second valve may be included in the housing including a second slidable member. The unit forms a double check valve protected by a filter means resulting in a reliable and maintenance free fluid control mechanism.

It is therefore an object of the present invention to provide a fluid control mechanism to selectively stop the flow of a fluid under pressure and to eliminate contamination of the flow system by particulate matter thereby insuring stoppage of the fluid flow as desired.

It is another object of the present invention to provide a fluid control mechanism usable with high pressure liquid chromatographic systems as an aid in obtaining accurate results therefrom.

It is yet another object of the present invention to provide a fluid control mechanism compatable with a liquid head of a reciprocating positive displacement pump.

It is a further object of the present invention to provide a fluid control mechanism having a reliable double check valve mechanism and a filter means forming a unit insertable within a housing, itself compatable with a chromatographic pumping system.

The invention possesses other objects and advantages especially as concerns particular features and characteristics thereof which will become apparent as the specification continues.

Various aspects of the present invention will evolve from the following detailed description of the preferred embodiments thereof which should be taken in conjunction with the accompanying drawings.

BRIEF DESCRIPTION OF THE DRAWINGS

FIG. 1 is an elevational cross-sectional view of the mechanism.

FIG. 2 is a bottom view of the device.

FIG. 3 is a top view of the device.

DESCRIPTION OF THE PREFERRED EMBODIMENTS

The flow control mechanism as a whole is shown in the drawings and is identified by reference character 10. Mechanism 10 includes as one of its elements a housing or valve housing 12. Housing 12 forms about an opening 14 which passes therethrough from the top portion 16 of housing 12 to the bottom portion 18 thereof. An external threaded portion 20 of housing 12 allows the threading insertion of housing 12 within a pump fitting internally threaded to accept the same. Housing 12 is of rigid construction using a material such as stainless steel to effect this chracteristic. Internally threaded portion 22 accepts threaded fittings of conduits, tubes, pipes and the like to further transport the fluid being pumped to a desired location. As shown, fluids would normally travel through opening 14 at the bottom portion 18 to the opening at the top portion 16 of housing 12. The housing further includes a first chamber 24 which may be created from the internal walls of opening 14. As depicted in FIG. 1 the first chamber 24 is within first slidable member 26 which may also be fashioned of stainless steel. In other words, in the basic embodiment of the invention, housing 12 and first slidable member 26 may be integrally formed. First chamber 24 communicates with opening 14. FIG. 3 indicates that top portion 16 may have a hexagonal configuration 28 to permit turning of the housing with a similarly shaped wrench. Gasket space 30 may house seal forming items associated with the aforesaid conduits and fittings. Funnel portion 32 of opening 14 affords reduction in the diameter opening 14 as desired.

A first seat 34 positions within housing opening 14 adjacent to first slidable member 26 which includes a circular recess 36. A restricted passage communicates with first chamber 24 and housing opening 14. For liquid chromatography applications the seat may be constructed of ruby or sapphire. The same materials may be employed to form first plug 40, which may externalize in a spherical object confined to first chamber 24. First plug or ball 40 is adapted to occupy first seat 34 and close the restricted passage 38 therethrough under fluid pressure in the direction from top portion 16 to the bottom portion 18 of housing 12. Thus, a first valve 44 is formed by first plug 40 to check the flow of fluid in one direction since first plug 40 will only close first seat 34.

Filter means 44 positions snuggly beneath first seat 34 and first slidable member 26. The presence of particulate matter in the vicinity of first seat 34 and first plug 40, such as solvent impurities, dust, metallic particles from the pump piston, burrs, chips from conduits and seals, will greatly impair the working of the first valve 42. The filter means 44 includes a pressure deformable section 46 which fits tightly within housing opening 14 beneath first seat 34 and first slidable member 26. Pressure deformable section may be constructed of Teflon, Kel-F, and other like plastics. A passage 48 cuts through the central portion of pressure deformable section 46, thus communicating with the housing opening 14. The bottom face 50 of pressure deformable section 46 may protrude from housing opening 14 below the bottom fact 52 of housing 12, FIGS. 1 and 2. A relatively rigid filter element 54 positions within the passage 48 of the pressure deformable section of filter means 44. The rigid filter element 54 could be sized a little larger than the passage 48 and forced into place under pressure. For example, rigid filter element 59 may be formed of sintered stainless steel, ceramic and other similar materials filtering particles of about two microns for liquid chromatography applications. Metallic powders exhibit relatively poor fatique life and will not withstand repeated reverse bending. Therefore, filter element 54 occupies only a portion of passage 48 leaving a gap 56 within passage 48 between the upper portion of filter element 54 and the upper portion of pressure deformable section 46. The placement of the mechanism 10 in a pump head will create pressure on the bottom face 52 of filter means 44, shown by directional arrows on FIG. 1. Deformable section 46 will cold flow onto the bottom face 52 of housing 12 into area 58, shown in phantom on FIG. 1. First slidable member 26, first seat 34 will move upwardly into a tighter fit within housing opening 14. Deformable member will also very tightly seal the wall of housing opening 14 against leakage of fluid therebetween. Filter element 54 will tend to fill gap 56 but will not be strained thereby.

The mechanism may also include first washer 60 composed of Teflon, Kel-F or other like material. Washer 60 bears on first slidable member 26 which is somewhat rigid.

A second valve 62 may be added to mechanism 10 to provide a double check valve operation. In this regard, second valve 62 includes second seat 64, second chamber 66, second slidable member 68 and second plug 20. A second washer 72 may be placed within housing opening 14 to bear on second slidable member 68.

In operation, valves 42 and 62 separated by washers 72 and 60 and filter means 44 form a unit which may be placed within housing opening 14. Pressure deformable section 46 may protrude from the housing at this time. The exertion of pressure on the bottom faces 50 and 52 of filter means 44 and housing 12 may come about as a result of the threading engagement of externally threaded portion 20 in a pump head. Deformable section 46 and washers 72 and 60 prevent leakage of fluid between the wall of opening 14 and the extremities of those elements. Internally threaded portion 22 would be connected to conduits and the like leading to a particular outlet. Fluid enters passage 48, passes through filter element 54 with the removal of extraneous particulate matter. The fluid continues through restricted passage 38 first chamber 24 and the center of washer 60. At this point the fluid enters second valve 62 via the restricted passage of second seat 64. After flowing through second chamber 66 and the center of washer 60, the fluid passes from housing opening 14 to its delivery point. Fluid pressure in the opposite direction will not result in fluid flow because of the seating of first and second plugs 40 and 70 in seats 34 and 64.

While in the foregoing specification embodiments of the invention have been set forth in considerable detail for purposes of making a complete disclosure of the invention, it will be apparent to those skilled in the art that numerous changes may be made in such details without departing from the spirit and principles of the invention.

What is claimed is:

1. A fluid control mechanism for use in a high pressure fluid system comprising:
   a. housing having an opening therethrough, said housing having a first chamber communicating with said opening, and having at least one exterior face adjacent said opening;
   b. a first seat positioned within said housing opening, said first seat including a restricted passage therethrough communicating with said first chamber and said housing opening;
   c. a first plug disposed within said first chamber, said first plug adapted to occupy said first seat and close said restricted passage through said first seat;
   d. filter means for preventing passage of particulate matter through said first chamber and said first seat restricted passage, said filter means comprising a pressure deformable section sized to tightly fit within said housing opening and protruding from said housing opening to the exterior of said housing, said pressure deformable section being adapted to cold flow to said exterior housing face upon the application of pressure on said pressure deformable section, said pressure deformable section having an opening therethrough communicating with said housing opening, said filter means further comprising a relatively rigid filter element disposed in said passage of said pressure deformable section to completely intercept fluid flow through said passage, said filter element occupying a portion thereof adjacent said exterior face and forming a gap therein opposite the portion of said pressure deformable section passage adjacent said housing exterior face, said filter element adapted for at least partially filling said gap upon said application of pressure on said pressure deformable section;

e. pump means for forcing high pressure fluid through said filter means, said housing adapted for engagement with said pump means, said engagement of said pump means with said housing providing said application of pressure on said pressure deformable section.

f. liquid chromatographic means for performing liquid chromatographic separations, said liquid chromatographic means receiving the high pressure fluid from said filter means.

2. The fluid control mechanism of claim 1 in which said first plug comprises a spherical member.

3. The fluid control mechanism of claim 1 which additionally comprises a first slidable member disposed within said housing, said first slidable member providing said first chamber.

4. The fluid control mechanism of claim 3 which additionally comprises a first washer bearing on said first slidable member within said housing opening.

5. The fluid control mechanism of claim 1 which additionally includes:
 a. second slidable member disposed within said housing, said second slidable member providing a second chamber;
 b. second seat positioned within said housing opening, said second seat including a restricted passage therethrough communicating with said second chamber and said housing opening;
 c. second plug disposed within said second chamber said second plug adapted to occupy said second seat and close said restricted passage therethrough;
 d. second washer bearing on said second slidable member within said housing opening.

6. The fluid control mechanism of claim 5 which additionally includes a first washer bearing on said first slidable member and bearing selectively on said second slidable member and said second seat, said first and second washers being compressible to permit sliding of said first and second slidable members and to permit retraction of said deformable section to a disposition at least substantially flush with said exterior of said housing.

7. The fluid control mechanism of claim 6 in which said first and second plugs comprise a spherical member.

8. The fluid control mechanism of claim 7 in which said exterior housing includes a threaded portion for threadingly engaging a fluid forcing apparatus.

9. A filter system for particulate matter in flowing fluids under high pressure comprising:
 a. housing having an opening therethrough, said housing having a chamber communication with said opening and having at least one exterior face adjacent said opening;
 b. a pressure deformable section sized to tightly fit within said housing opening and protruding from said housing opening to the exterior of said housing, said pressure deformable section being adapted to cold flow to said exterior housing face upon the application of pressure on said pressure deformable section, said pressure deformable section having an opening therethrough communicating with said housing opening;
 c. a relatively rigid filter element disposed in said passage of said pressure deformable section to completely intercept fluid flow through said passage, said filter element occupying a portion thereof and forming a gap therein, said filter element adapted for at least partially filling said gap upon the application of pressure on said pressure deformable section;
 d. pump means for forcing high pressure fluid through said filter means, said housing adapted for engagement with said pump means, said engagement of said pump means with said housing providing said application of pressure on said pressure deformable section.
 e. liquid chromatographic means for performing liquid chromatographic separations, said liquid chromatographic means receiving the high pressure fluid leaving said filter element.

* * * * *